United States Patent [19]

Hayashi et al.

[11] Patent Number: 5,462,958

[45] Date of Patent: Oct. 31, 1995

[54] BENZENE DERIVATIVES AND METHOD OF TREATING ARTERIOSCLEROSIS WITH BENZENE DERIVATIVES

[75] Inventors: Kenji Hayashi; Nobuhisa Watanabe; Koichi Nose; Hiroshi Tanaka; Issei Ohtsuka; Motoji Kokushi; Hironobu Hiyoshi; Hiroko Kobayashi; Toshie Yamada; Toru Horie, all of Ibaraki, Japan

[73] Assignee: Eisai Co., Ltd., Tokyo, Japan

[21] Appl. No.: 182,061

[22] PCT Filed: Jul. 12, 1993

[86] PCT No.: PCT/JP93/00961

§ 371 Date: May 19, 1994

§ 102(e) Date: May 19, 1994

[87] PCT Pub. No.: WO94/02452

PCT Pub. Date: Mar. 2, 1994

[30] Foreign Application Priority Data

Jul. 20, 1992 [JP] Japan ..................... 4-213242
Sep. 30, 1992 [JP] Japan ..................... 4-283432

[51] Int. Cl.⁶ .............. A61K 31/415; A61K 31/195; C07C 275/34; C07D 233/60
[52] U.S. Cl. .............. 514/399; 514/535; 514/568; 548/342.5; 560/34; 562/439
[58] Field of Search ........... 548/342.5; 562/471, 562/439; 514/399, 535, 568; 560/34

[56] References Cited

U.S. PATENT DOCUMENTS

| | | | |
|---|---|---|---|
| 3,925,387 | 12/1975 | Maruyama et al. | 514/596 |
| 4,623,662 | 11/1986 | De Vries | 514/596 |
| 4,824,843 | 4/1989 | Hoefle et al. | 514/228.8 |

FOREIGN PATENT DOCUMENTS

| | | | |
|---|---|---|---|
| 0074130 | 3/1983 | European Pat. Off. | 548/342.5 |
| 0245687 | 11/1987 | European Pat. Off. | |
| 0283742 | 9/1988 | European Pat. Off. | |
| 0344425 | 12/1989 | European Pat. Off. | |
| 0354994 | 2/1990 | European Pat. Off. | |
| 0418071 | 3/1991 | European Pat. Off. | |
| 477778 | 1/1992 | European Pat. Off. | |
| 0559898 | 9/1993 | European Pat. Off. | |
| 0561175 | 9/1993 | European Pat. Off. | |
| 2162168 | 7/1973 | France. | |
| 2259004 | 6/1973 | Germany. | |
| 2056968 | 3/1981 | United Kingdom. | |
| 2113684 | 8/1983 | United Kingdom. | |

OTHER PUBLICATIONS

T. Kimura et al., *Journal of Medicinal Chemistry*, May, 1993, vol. 36, 1641–1653.
Cross et al., J. Med. Chem., vol. 28, pp. 1427–1432, 1985.
Chemical Abstracts, No. 117176d, vol. 119, No. 11, Sep. 13, 1993, p. 924.
J. Med. Chem., vol. 21, No. 10, 1989 (pp. 2318–2325).
Database WPI, Derwent Publications Ltd., London, GB AN 81-38689D & GB-A-2 062 622 (American Cyanamid Co., Week 8122) 1981.

Primary Examiner—Jacqueline Haley
Attorney, Agent, or Firm—Birch, Stewart, Kolasch & Birch

[57] ABSTRACT

The present invention provides a novel benzene derivative useful as a preventive and medically treating medicine for arteriosclerosis, and a cholesterol O-acyl transferase inhibitor comprising the benzene derivative as an active ingredient.

The benzene derivative according to the present invention is represented by the following general formula (I):

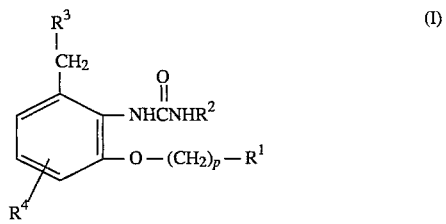

wherein $R^1$ represents a carboxyl group which may be protected or a group represented by the formula:

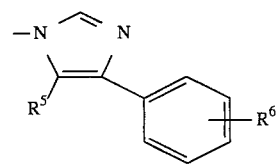

wherein $R^5$ represents a lower alkyl group or a hydroxyalkyl group and $R^6$ represents a hydrogen atom or a hydroxyl group; $R^2$ represents a hydrogen atom, a lower alkyl group or the like; $R^3$ and $R^4$ each represent a hydrogen atom or a hydroxyl group; and p is an integer of 1 to 6.

7 Claims, No Drawings

BENZENE DERIVATIVES AND METHOD OF TREATING ARTERIOSCLEROSIS WITH BENZENE DERIVATIVES

This application is a National Stage Application of PCT/JP93/00961, filed Jul. 12, 1993 and published on Feb. 3, 1994 as WO/94/02452.

FIELD OF THE INVENTION

The present invention relates to a benzene derivative or a pharmacologically acceptable salt thereof which is useful as a medicine.

DESCRIPTION OF THE RELATED PRIOR ART

Cerebrovascular diseases such as cerebral apoplexy and myocardial infarction which rank high in the list of death causes in Japan are mostly caused by arteriosclerosis as its terminal symptoms. The number of patients with arteriosclerosis has steadily increased with the westernization of eating habits and the increase in the aged population and accordingly the number of patients with cerebral apoplexy and myocardial infarction also keeps on increasing.

As is well known, the lethality of patients with cerebral apoplexy and myocardial infarction is extremely high and even if these patients avoid death, many of them suffer from serious sequelae.

Accordingly, it is extremely important to prevent or medically treat arteriosclerosis before these serious diseases are caused.

Although antihypolipidemic medicines which are effective in lowering the content of lipid, particularly cholesterol in the blood have hitherto been mainly used for the prevention and medical treatment of arteriosclerosis, no decisively effective medicine has been found as of yet, so that various studies are now in progress on arteriosclerosis and preventive and medically treating medicines therefor.

Recently, it has been found that cholesterol O-acyl transferase (or acyl-CoA: cholesterol O-acyl transferase) (hereinafter abbreviated to "ACAT") present in the arterial wall participates in the formation of fat striae which are observed in arteriosclerosis (atherosclerosis).

More precisely, it has been clarified that the excess accumulation of cholesterol ester on the arterial wall is causative of atheromatous lesion and the formation of cholesterol ester is catalyzed by the ACAT.

Accordingly, it is expectable that the inhibition of the ACAT may control the excess accumulation of cholesterol ester on arterial wall to thereby depress the formation and evolution of artheromatous lesion.

Meanwhile, the ACAT is also known to participate in the intestinal absorption of cholesterol. Specifically, dietary cholesterol and cholesterol released into the intestines by the adaptation of a living body itself in a state mixed with bile are absorbed as free cholesterol from the intestines, esterified by the action of ACAT, packed into chylomicrons and released into the blood.

Accordingly, since the free cholesterol absorbed from the intestines is saturated by the inhibition of the ACAT in intestines, it is expectable that the intestinal absorption of cholesterol may be controlled.

Although compounds exhibiting an inhibitory activity against ACAT have been proposed in, for example, U.S. Pat. Nos. 4,628,662, 4,489,094, 4,489,090, 4,824,848 and 4,285,951 and Japanese Patent Publication-A Nos. 184070/1988, 281058/1984, 41655/1985, 277851/1987, 258866/1987, 28848/1988, 258060/1988, 19016/1989, 93569/1989, 208860/1989, 6455/1990, 6457/1990 and 6456/1990, these compounds are different from compounds of the present invention in the chemical structures.

DISCLOSURE OF THE INVENTION

The present inventors have extensively studied for many years on a compound which exhibits an inhibitory activity against ACAT of the arterial wall and the intestines to thereby hinder the excess accumulation of cholesterol ester on the arterial wall and the intestinal absorption of cholesterol with their attentions being paid to ACAT. As a result, they have found that a specific benzene derivative or a pharmacologically acceptable salt thereof can attain the object as will be described below. The present invention has been accomplished on the basis of this finding.

The compound of the present invention is a benzene derivative represented by the following general formula (I) or a pharmacologically acceptable salt thereof:

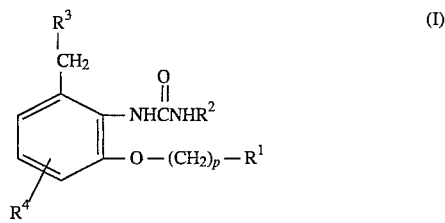

[wherein $R^1$ represents a carboxyl group which may be protected or a group represented by the formula:

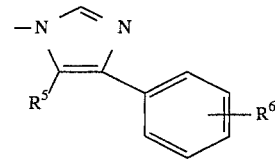

(wherein $R^5$ represents a lower alkyl group or a hydroxyalkyl group and $R^6$ represents a hydrogen atom or a hydroxyl group);

$R^2$ represents a hydrogen atom, a lower alkyl group, a hydroxyalkyl group or a carboxyalkyl group;

$R^3$ and $R^4$ each represent a hydrogen atom or a hydroxyl group; and p is an integer of 1 to 6.].

The compound of the present invention represented by the above general formula (I) has a specific inhibitory activity against ACAT which is one of the enzymes participating in the formation of foam cells and therefore can inhibit the evolution of arteriosclerosis.

Accordingly, the present invention relates to an ACAT inhibitor and a preventive and medically treating medicine for diseases for which an ACAT inhibiting action is efficacious, for example, arteriosclerosis, which comprises a benzene derivative represented by the above general formula (I) or a pharmacologically acceptable salt thereof as an active ingredient.

Further, the present invention relates a pharmacological composition comprising a preventively or therapeutically effective amount of a benzene derivative represented by the above general formula (I) or a pharmacologically acceptable salt thereof and a vehicle, a use of a benzene derivative represented by the above general formula (I) or a pharmacologically acceptable salt thereof for the making of a medicament for medically treating a disease for which an ACAT inhibiting action is efficacious, and a method for treating a disease which comprises administering a therapeutically effective amount of a benzene derivative represented by the above general formula (I) or a pharmacologically acceptable salt thereof to a patient suffering from a disease for which an ACAT inhibiting action is efficacious.

The present invention will be described in detail hereinafter.

In the definition of the above general formula (I), the lower alkyl group defined with respect to $R^2$ and $R^5$ is a straight chain- or branched one having 1 to 6 carbon atoms and examples thereof include methyl group, ethyl group, n-propyl group, isopropyl group, n-butyl group, isobutyl group, sec-butyl group, tert-butyl group, n-pentyl group, isopentyl group, neopentyl group, tert-pentyl group, 2-methylbutyl group, n-hexyl group, isohexyl group, 2-methylpentyl group, 8-methylpentyl group, 2,2-dimethylbutyl group, 2,3-dimethylbutyl group, 3,3-dimethylbutyl group, 2-ethylbutyl group, 3-ethylbutyl group, 1-ethyl-1-methylpropyl group and 1-ethyl-2-methylpropyl group, among which methyl group, ethyl group, n-propyl group, n-butyl group and so on are preferably cited.

The carboxyl group which may be protected as defined with respect to $R^1$ is a free carboxyl group, or a carboxyl group protected with a lower alkyl group represented by methyl group or ethyl group, a halogenoalkyl group such as 2,2,2-trichloroethyl group, 2-iodoethyl group and trichloromethyl group, a lower alkanoyloxyalkyl group such as pivaloyloxymethyl group, 1-acetoxyethyl group and 2-acetoxyethyl group, a heterocyclic group such as a 3-phthalidyl group or the like. Further, the protected carboxyl group also includes various acid amide groups. In short, the protected carboxyl group may be any one so far as it can be decomposed into a carboxyl group in vivo by any means.

The hydroxyalkyl group defined with respect to $R^2$ and $R^5$ means a lower alkyl group as described above wherein any of the carbon atoms has one or two hydroxyl groups.

Representative processes for preparing the compound of the present invention will be described hereinafter.

Preparation process 1

The compound represented by the general formula (I) can be prepared by the following process:

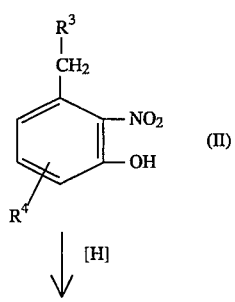

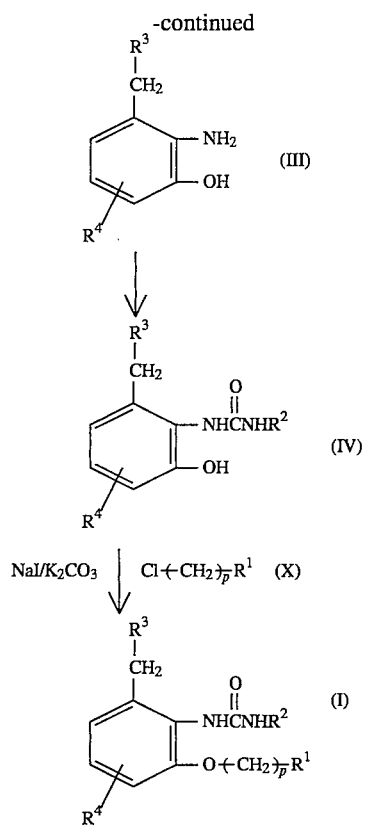

(wherein $R^1$, $R^2$, $R^3$, $R^4$ and p are each as defined above.)

More specifically, the objective compound (I) can be prepared by catalytically hydrogenating a nitro compound represented by the general formula (II) into an aniline compound represented by the general formula (III) in a conventional manner, converting the aniline compound (III) into a urea compound (IV) in a conventional manner, and finally condensing the urea compound (IV) with a compound represented by the general formula (X).

It is preferred to use a palladium-carbon catalyst in the conversion of the nitro compound (II) into the aniline compound (III).

The conversion of the aniline compound (III) into the urea compound (IV), though it may be conducted by any conventional process, is preferably conducted by a process which comprises reacting the aniline compound (III) with sodium cyanate in an acetic acid-water medium or by a process which comprises reacting the aniline compound (III) with an isocyanate in a solvent inert to the reaction, e.g., tetrahydrofuran.

The objective compound (I) can be prepared by condensing the urea compound (IV) thus obtained with a compound represented by the general formula (X) in a conventional manner. The condensation is preferably conducted in the presence of sodium iodide and potassium carbonate. Although the solvent to be used in the condensation may be any one inert to the reaction, it is preferably, e.g., dimethylformamide. The reaction temperature is preferably about 80°.

Preparation process 2

The compound represented by the general formula (I) can also be prepared by the following process:

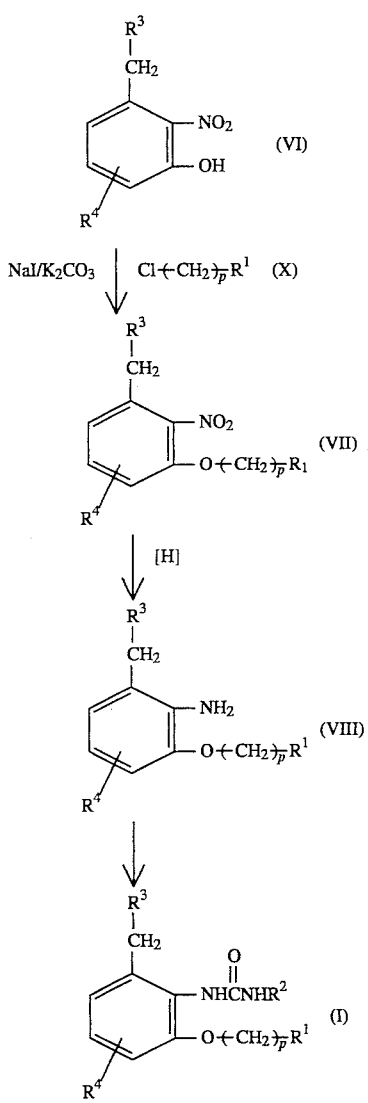

(wherein $R^1$, $R^2$, $R^3$, $R^4$ and p are each as defined above.)

More precisely, the objective compound (I) is prepared by condensing a compound represented by the general formula (VI) with a compound represented by the general formula (X) in a conventional manner to give a compound represented by the general formula (VII), catalitically hydrogenating the obtained compound represented by the general formula (VII) into an aniline compound represented by the general formula (VIII), and converting the aniline compound (VIII) into the objective compound (I) in a conventional manner.

The solvent to be used in the condensation of the compound represented by the general formula (VI) with the compound represented by the general formula (X) is preferably dimethylformamide and the like, though it may be any one inert to the reaction.

The obtained compound represented by the general formula (VII) is catalytically hydrogenated into the compound represented by the general formula (VIII) in a conventional manner and the catalyst to be used in this step is preferably a palladium-carbon catalyst.

The objective compound (I) can be prepared from the obtained aniline compound represented by the general formula (VIII) preferably by a process which comprises reacting the aniline compound (VIII) with sodium cyanate in an acetic acid-water medium or a process which comprises reacting the aniline compound (VIII) with an isocyanate in a solvent inert to the reaction, e.g., tetrahydrofuran.

In the present invention, the "pharmacologically acceptable salt" is not limited. Examples thereof includes an alkali metal salt such as sodium salt and potassium salt; ammonium salt; a quaternary ammonium salt such as tetraethylammonium salt and betaine salt; an alkaline earth metal salt such as calcium salt and magnesium salt; an inorganic acid salt such as hydrochloride, hydrobromide, hydroiodide, sulfate, carbonate, hydrogencarbonate; an organic carboxylic acid salt such as acetate, maleate, lactate and tartrate; an organic sulfonate such as methanesulfonate, hydroxymethanesulfonate, hydroxyethanesulfonate, taurine salt, benzenesulfonate and toluenesulfonate; an amino acid salt such as arginine salt, lysine salt, serine salt, aspartic acid salt, glutamic acid salt and glycine salt; an amine salt such as trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt and phenethylbenzylamine salt.

Next, experimental example will be given to illustrate the effect of the compounds of the present invention in detail.

Experimental Example

1. Experimental method
<in-vitro test>

Representative compounds according to the present invention were examined for ACAT-inhibitory activity according to the in-vitro test method described in Journal of Lipid Research, vol. 24, pp. 1049–1059 (1983) by F. J. Field and S. N. Mathur.

The inhibitory activity of a test compound against the acylation, which was based on the inhibitory activity of the test compound against the enzyme which catalyzes the acylation of cholesterol with oleoyl-CoA, was evaluated by using one of the supernatant of homogenate of the arterial wall of a rabbit, the microsome of the small intestine of a rat and the supernatant of homogenate of the epithelial cell ($CaCO_2$) resulting from human colon cancer as an enzyme source, determining the amount of a radioisotope-labeled cholesterol oleate made from a radiolabeled oleoyl-CoA and (free) cholesterol and comparing the result of the case when a test compound was added with the result of control (the case when no test compound was added).

The results are given in Table 1. The data which are given in Table 1 are $IC_{50}$ values, i.e., the concentrations of test compounds necessary for inhibiting 50% of the enzymatic activity of ACAT.

TABLE 1

| Test Compound (Ex. No.) | ACAT-inhibitory activity $IC_{50}$ (µM) | | |
|---|---|---|---|
| | rat | rabbit | $CaCO_2$ |
| 1 | — | 0.58 | 1.1 |
| 2 | — | 6.9 | 1.0 |
| 5 | 0.15 | 0.85 | 0.17 |
| 6 | — | 3.8 | — |
| 8 | — | — | 3.5 |
| 9 | 0.084 | 0.7 | 0.32 |
| 10 | 4.2 | 1.0 | 0.48 |
| 11 | 0.068 | 0.26 | 0.10 |

It is clarified from the above results that the compounds of the present invention exhibit an ACAT inhibitory activity. Accordingly, the compounds of the present invention are useful as medically treating medicines for diseases for which an ACAT inhibiting action is efficacious. In other words, the compounds of the present invention are useful as preventive and medically treating medicines for various arterioscleroses. Particularly, they are effective as preventive and medically treating medicines for diseases caused by arteriosclerosis, for example, cerebrovascular diseases such as cerebral apoplexy and cardiac infarction. Further, the compounds of the present invention are lowly toxic, being therefore highly safe. The present invention is highly valuable also in this respect.

When the compound of the present invention is administered to a patient as an anti-arteriosclerotic medicine, it may be orally administered in the form of powder, granule, capsule or syrup or may be parenterally administered as suppository, injection, external preparation or drop. The dose per adult a day is generally about 0.1 to 5,000 mg, preferably 2 to 1,000 mg, which is administered at once or in several portions, though the dosage remarkably varies depending upon the symptom, the age and so on.

The pharmaceutical preparation is prepared by using a conventional vehicle for preparation according to a conventional process.

More specifically, a solid preparation for oral administration is prepared by adding a vehicle and, if necessary, a binder, a disintegrator, a lubricant, a coloring matter and/or a corrective to a basis and shaping the obtained mixture into tablet, coated tablet, granule, powder or capsule according to a conventional manner.

The vehicle to be used includes, for example, lactose, corn starch, sucrose, glucose, sorbitol, crystalline cellulose and silicon dioxide; the binder to be used includes, for example, polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin; the lubricant to be used includes, for example, magnesium stearate, talc, polyethylene glycol, silica and hardened vegetable oils; the coloring matter to be used includes those permitted to be added to medicines; and the corrective to be used includes powdered cocoa, menthol, aromatic powder, mentha oil, borneol and powdered cinnamon bark. The tablet and granule prepared with the use of them may be, of course, coated with sugar, gelatin or the like at need.

An injection is prepared by adding a pH modifier, a buffer, a stabilizer and/or a solubilizing agent to a basis at need and formulating the obtained mixture into a subcutaneous, intramuscular or intravenous injection according to a conventional manner.

EXAMPLES

Examples of the present invention will be described hereinafter, though it is needless to say that the present invention is not limited to them.

Example 1

N-Butyl-N'-[2-[3-(5-ethyl-4-phenyl-1H-imidazol-1-yl)propoxy]-4-hydroxy-6-methylphenyl]urea

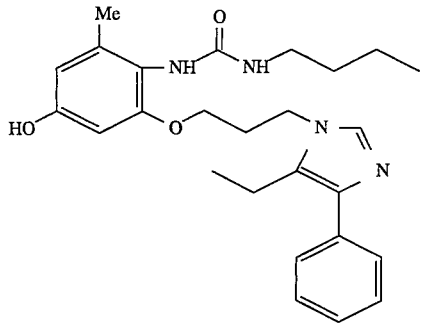

1 g (4.2 mmol) of N-butyl-N'-(2,4-dihydroxy-6-methylphenyl)urea was dissolved in 5 ml of dimethylformamide, followed by the addition of 1.45 g (10.5 mmol) of potassium carbonate, 5 ml of a solution of 1.04 g (4.2 mmol) of 1-(3-chloropropyl)-5-ethyl-4-phenylimidazole in dimethylformamide and a catalytic amount of sodium iodide. The obtained mixture was stirred at 80° C. for 2 hours.

The obtained reaction mixture was neutralized with dilute hydrochloric acid and extracted with ethyl acetate. The ethyl acetate phase was washed with water and dried over anhydrous magnesium sulfate. Then, ethyl acetate was distilled off in a vacuum.

The obtained residue was purified by silica gel column chromatography (solvent: benzene/acetone) and recrystallized from ethyl acetate to give 0.23 g of the title compound. Yield: 12.0%.

m.p.: 200°~201° C.
M/Z (M+1)$^+$: 450
$^1$H-NMR (DMSO-d$_6$)
δ(ppm)=0.82 (3H, t, J=7 Hz ) 1.17 (3H, t, J=7 Hz) 1.18~1.40 (4H, m) 2.00~2.15 (2H, m) 2.07 (3H, s) 2.76 (2H, q, J=7 Hz) 2.92~3.05 (2H, m) 3.80 (2H, t, J=6Hz) 4.10 (2H, t, J=6 Hz ) 5.99 (1H, brs) 6.18 (2H, s) 6.84 (1H, s) 7.14~7.61 (6H, m) 9.19 (1H, s)

Example 2

N-Butyl-N'-[2-[3-[5-ethyl-4-(4-hydroxyphenyl)-1H-imidazol-1-yl]propoxy]-6-methylphenyl]urea

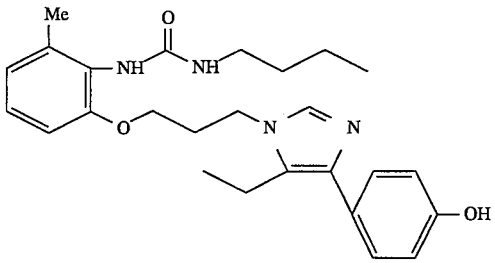

0.8 g (1.48 mmol) of the N-butyl-N'-[2-[3-[5-ethyl-4-(4-benzyloxyphenyl)-1H-imidazol-1-yl]propoxy]-6-methylphenyl]urea prepared in a similar manner to that of the Example 1 was dissolved in a mixture comprising 50 ml of tetrahydrofuran and 20 ml of ethanol and hydrogenated in the presence of a palladium-carbon catalyst overnight. The palladium-carbon catalyst was filtered out and the filtrate was concentrated in a vacuum. The residue was recrystallized from ethyl acetate to give 0.51 g of the title compound. Yield: 76.6%.

m.p.: 188°~190° C.
M/Z (M+1)$^+$: 451
$^1$H-NMR (DMSO-d$_6$)
δ(ppm)=0.90 (3H, s, J=7 Hz) 1.12 (3H, s, J=7 Hz) 1.20~1.40 (4H, m) 2.05~2.14 (2H, m) 2.16 (3H, s) 2.70 (2H, q, J=7 Hz) 2.98~3.07 (2H, m) 3.89 (2H, t, J=6 Hz) 4.08 (2H, t, J=6 Hz) 6.15~6.24 (1H, m) 6.72~7.52 (9H, m) 9.30 (1H, brs)

Example 3

N-[2-[3-[5-Ethyl-4-(4-hydroxyphenyl)-1H-imidazol-1 -yl]propoxy]-6-methylphenyl]urea

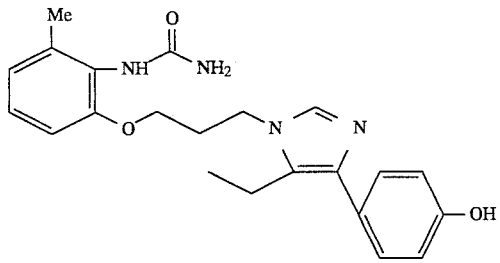

The title compound was prepared in a similar manner to that of the Example 2. Yield: 64.6%.
m.p.: 174°~175° C.
M/Z (M+1)$^+$: 395
$^1$H-NMR (DMSO-d$_6$)
δ(ppm)=1.15 (3H, t, J=7 Hz) 2.05~2.16 (2H, m) 2.17 (3H, s) 2.72 (2H, q, J=7 Hz) 3.90 (2H, t, J=6 Hz) 4.10 (2H, t, J=6 Hz) 5.80 (2H, brs) 6.70~7.52 (8H, m) 8.29 (1H, s)

Example 4

N-[2-[3-[5-(1,2-Dihydroxyethyl)-4-phenyl-1H-imidazol-1-yl]propoxy]-6-methylphenyl]urea

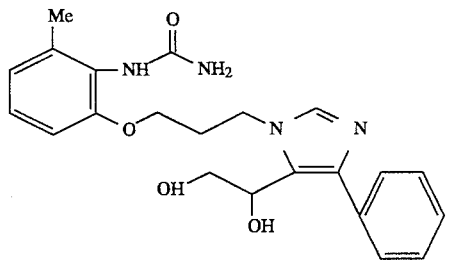

0.23 g (0.61 mmol) of the N-[2-[3-(5-vinyl-4-phenyl-1H-imidazol-1-yl)propoxyl-6-methylphenyl]urea prepared in a similar manner to that of the Example 1 was dissolved in 10 ml of tetrahydrofuran, followed by the addition of 2 ml of distilled water, a catalytic amount of osmium tetraoxide and 0.08 g (0.67 mmol) of 4-methylmorpholine N-oxide at room temperature. The obtained mixture was stirred overnight.

An aqueous solution of sodium hydrogensulfite was added to the reaction mixture and the obtained mixture was stirred for 30 minutes and extracted with ethyl acetate twice. The ethyl acetate phase was washed with water and dried over anhydrous magnesium sulfate. Then, ethyl acetate was distilled off in a vacuum. The obtained residue was purified by silica gel chromatography (solvent: dichloromethane/methanol) and recrystallized from ethyl acetate to give 0.024 g of the title compound. Yield: 9.9% m.p.: 160°~162° C. M/Z (M+1)$^+$: 411
$^1$H-NMR (DMSO-d$_6$)
δ(ppm)=2.20 (3H, s) 2.20~2.80 (2H, m) 3.55~3.65 (1H, m) 3.70~8.80 (1H, m) 3.90~4.00 (2H, m) 4.24~4.40 (2H, m) 4.92~5.00 (2H, m) 5.60 (1H, d, J=5 Hz) 5.81 (2H, brs) 6.78~7.76 (10H, m)

Example 5

N-Butyl-N'-[2-[3-[5-(1-hydroxyethyl)-4-phenyl-1H-imidazol-1-yl]propoxy]-6-methylphenyl]urea

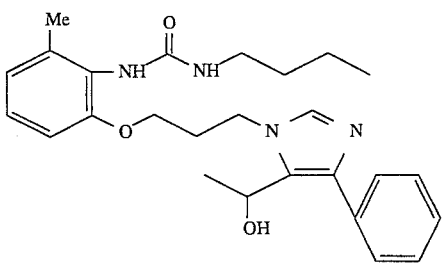

120 mg (0.27 mmol) of the N-butyl-N'-[2-[3-(5-acetyl-4-phenyl-1H-imidazol-1-yl)propoxy]-6-methylphenyl]urea prepared in a similar manner to that of the Example 1 was dissolved in 5 ml of methanol, followed by the addition of 15 mg (0.40 mmol) of sodium borohydride at room temperature. The obtained mixture was stirred overnight. After the decomposition and neutralization of excess sodium borohydride with dilute hydrochloric acid, the resulting mixture was extracted with ethyl acetate twice. The ethyl acetate phase was washed with water and dried over anhydrous magnesium sulfate. Then, ethyl acetate was distilled off in a vacuum. The obtained residue was purified by silica gel chromatography (solvent: dichloromethane/methanol) to give 65 mg of the title compound. Yield: 53.5% m.p.: amorphous
M/Z (M+1)$^+$: 451
$^1$H-NMR (CDCl$_3$)
δ(ppm)=0.84 (3H, t, J=7 Hz) 1.20~1.42 (4H, m) 1.59 (3H, d, J=7 Hz) 2.26 (3H, s) 2.26~2.40 (2H, m) 3.09~3.21 (2H, m) 3.94~4.06 (2H, m) 4.32~4.52 (2H, m) 4.98 (1H, brs) 5.25~5.35 (2H, m) 6.13 (1H, brs ) 6.69 (1H, d, J=7 Hz ) 6.84 (1H, d, J=7 Hz) 7.10 (1H, t, J=7 Hz ) 7.22~7.75 (6H, m)

Example 6

N-(4-Hydroxybutyl)-N'-[2-[3-(5-ethyl-4-phenyl-1H-imidazol-1-yl)propoxy]-6-methylphenyl]urea

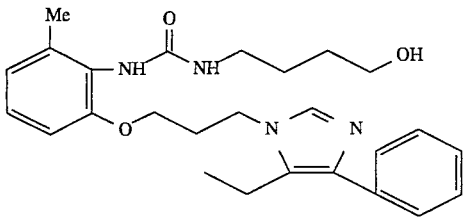

113 mg (23 mmol) of the N-(3-ethoxycarbonylpropyl)-N'-[2-[3-(5-ethyl-4-phenyl-1H-imidazol-1-yl)propoxy]-6-methylphenyl]urea prepared in a similar manner to that of the Example 1 was dissolved in 5 ml of tetrahydrofuran, followed by the addition of 13 mg (34 mmol) of lithium aluminum hydride under cooling with ice. The obtained mixture was stirred for one hour. 0.013 ml of water, 0.013 ml of a 15% aqueous solution of sodium hydroxide and 0.039 ml of water were added to the resulting mixture under cooling with ice, and then precipitates thus formed were filtrate out.

The filtrate was concentrated in a vacuum and the residue was purified by silica gel chromatography (solvent: benzene/acetone→acetone/methanol) and recrystallized from ethyl acetate/benzene/n-hexane to give 30 mg of the title compound Yield 29.0% m.p.: 164°~166° C.
M/Z (M+1)$^+$: 451
$^1$H-NMR (CDCl$_3$)
δ(ppm)=1.25 (3H, t, J=7 Hz) 1.48~1.84 (4H, m) 2.28 (3H, s) 2.22~2.36 (2H, m) 2.80 (2H, q, J=7 Hz) 3.14~3.30 (2H, m) 3.52~3.62 (2H, m) 3.99 (2H, t, J=6 Hz) 4.30 (2H, t, J=6 Hz) 5.70 (1H, brs) 6.40 (1H, brs) 6.68 (1H, d, J=7 Hz) 6.83 (1H, d, J=7 Hz) 7.07 (1H, t, J=7 Hz) 7.27~7.60 (5H, m) 8.19 (1H, brs)

Example 7

N-(3-Carboxypropyl)-N'-[2-[3-(5-ethyl-4-phenyl-1H-imidazol-1-yl)propoxy]-6-methylphenyl]urea

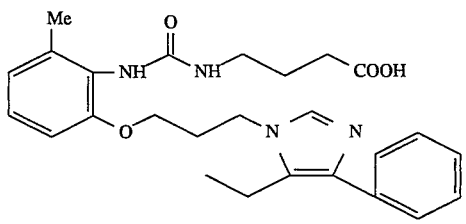

77 mg (16 mmol) of the N-(3-ethoxycarbonylpropyl)-N'-[2-[3-(5-ethyl-4-phenyl-1H-imidazol-1-yl)propoxy]-6-methylphenyl]urea prepared in a similar manner to that of the Example 1 was dissolved in 5 ml of ethanol, followed by the addition of 26 mg (47 mmol) of potassium hydroxide at room temperature. The obtained mixture was stirred overnight and extracted with ethyl acetate once. The aqueous phase was neutralized with dilute hydrochloric acid and extracted with ethyl acetate thrice. The ethyl acetate phase was washed with water and dried over anhydrous magnesium sulfate. Then, ethyl acetate was distilled off in a vacuum. The obtained residue was recrystallized from benzene/n-hexane to give 49 mg of the title compound. Yield: 66.0%.

m.p.: 201°~202° C.
M/Z (M+1)$^+$: 465
$^1$H-NMR (DMSO-d$_6$)
δ(ppm)=1.16 (3H, t, J=7 Hz) 1.55~1.68 (2H, m) 2.05~2.18 (2H, m) 2.18 (3H, s) 2.20~2.25 (2H, m) 2.78 (2H, q, J=7 Hz) 3.00~3.10 (2n, m) 3.90 (2H, t, J=6 Hz) 4.12 (2H, t, J=6 Hz) 6.30 (1H, brs) 6.75~7.61 (10H, m)

Example 8

N-[2-[3-(5-Ethyl-4-phenyl-1H-imidazol-1-yl)propoxy]-6-methylphenyl]urea

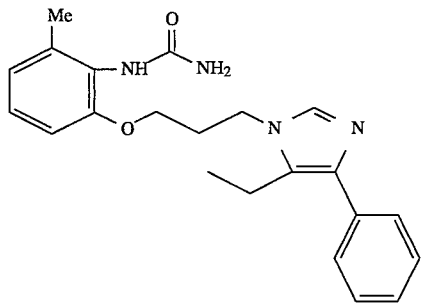

123 mg (0.37 mmol) of 2-[3-(5-ethyl-4-phenyl-1H-imidazol-1-yl)propoxy]-6-methylaniline was dissolved in a mixture comprising 1 ml of acetic acid and 2 m of water. A solution of 48 mg (0.74 mmol) of sodium cyanate in 1 ml of water was heated to 35° C. and dropped into the solution prepared above. The obtained mixture was stirred for 30 minutes, neutralized with an aqueous solution of sodium hydrogencarbonate, and extracted with ethyl acetate thrice. The ethyl acetate phase was washed with water and dried over anhydrous magnesium sulfate. Then, ethyl acetate was distilled off in a vacuum. The residue was recrystallized from benzene/n-hexane to give 24 mg of the title compound. Yield: 17.1% m.p.: 117°~119° C.
M/Z (M+1)$^+$: 379
$^1$H-NMR (CDCl$_3$)
δ(ppm)=1.22 (3H, t, J =7 Hz ) 2.20~2.32 (2H, m) 2.29 (3H, s) 2.78 (2H, q, J=7 Hz) 3.99 (2H, t, J=6 Hz ) 4.24 (2H, t, J=6 Hz) 5.07 (2H, brs) 6.43 (1H, brs) 6.67 (1H, d, J=7 Hz) 6.82 (1H, d, J=7 Hz) 7.09 (1H, t, J=7 Hz) 7.22~7.60 (5H, m) 7.97 (1H, brs)

Example 9

N-Butyl-N'-[2-[3-(5-ethyl-4-phenyl-1H-imidazol-1-yl)propoxy]-6-hydroxymethylphenyl]urea

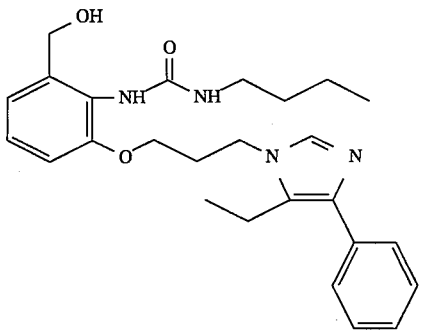

200 mg (0.57 mmol) of 2-[3-(5-ethyl-4-phenyl-1H-imidazol-1-yl)propoxy]-6-hydroxylmethylaniline was dissolved in 10 ml of tetrahydrofuran, followed by the addition of a solution of 62 mg (0.63 mmol) of n-butyl isocyanate in 10 ml of tetrahydrofuran. The obtained mixture was stirred at room temperature overnight.

The solvent was distilled off and the residue was recrystallized from ethyl acetate to give 90 mg of the title compound. Yield: 35.1%.
m.p.: 146°~147° C.
M/Z (M+1)⁺: 451
¹H-NMR (CDCl₃)
δ(ppm)=0.88 (3H, t, J=7 Hz) 1.19 (3H, t) 1.22~1.48 (4H, m) 2.30~2.40 (2H, m) 2.72 (2H, q, J=7 Hz) 3.11~3.20 (2H, m) 4.07 (2H, t, J=6 Hz) 4.20 (2H, t, J=6 Hz) 4.42 (2H, s) 6.09 (1H, brs) 6.43 (1H, brs) 6.68~7.95 (9H, m)

Example 10

N-(3-Hydroxybutyl)-N'-[2-[3-(5-ethyl-4-phenyl-1H-imidazol-1-yl)propoxy]-6-methylphenyl]urea

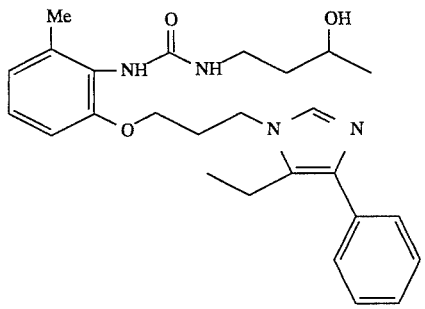

350 mg (0.60 mmol) of the N-(3-oxobutyl)-N'-[2 -[5-ethyl-4-phenyl-1H-imidazol-1-yl)propoxy]-6 -methylphenyl]urea prepared in a similar manner to that of the Example 9 was dissolved in 10 ml of methanol, followed by the addition of 34 mg (0.90 mmol) of sodium borohydride under cooling with ice. The obtained mixture was stirred at room temperature for 2 hours.

After the decomposition and neutralization of excess sodium borohydride with dilute hydrochloric acid, the resulting mixture was extracted with ethyl acetate twice. The ethyl acetate phase was washed with water and dried over anhydrous magnesium sulfate. Then, ethyl acetate was distilled off in a vacuum. The residue was purified by silica gel chromatography (solvent: dichloromethane/methanol) and recrystallized from ethyl acetate to give 54 mg of the title compound. Yield: 20.1%.
m.p.: 120°~122° C.
M/Z (M+1)⁺:451 p ¹H-NMR (CDCl₃)
δ(ppm)=1.13 (3H, t, J=7 Hz) 1.22 (3H, t, 7 Hz ) 1.35~1.55 (2H, m) 2.18~2.30 (2H, m) 2.28 (3H, s) 2.79 (2H, q, J=7 Hz) 3.00~3.10 (1H, m) 3.52~3.67 (1H, m) 3.73~3.86 (1H, m) 3.90~4.00 (2H, m) 4.11~4.23 (2H, m) 5.61 (1H, brs) 6.16 (1H, s) 6.67 (1H, d, J=7 Hz) 6.84 (1H, d, J=7 Hz) 7.08 (1H, t, J=7 Hz 7.22~7.78 (6H, m)

Example 11

N-Butyl-N'-[2-[3-(5-ethyl-4-phenyl-1H-imidazol-1-yl)propoxy]-5-hydroxy-6-methylphenyl]urea

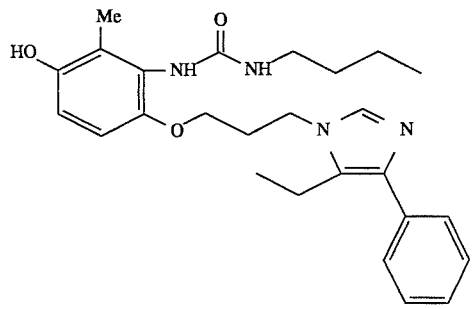

4.5 g (8.2 mmol) of the N-butyl-N'-[2-[3-(5 -ethyl-4-phenyl-1H-imidazol-1-yl)propoxy]-5-butylcarbamoyloxy-6-methylphenyl]urea prepared in a similar manner to that of the Example 9 was dissolved in 100 ml of ethanol, followed by the addition of 1.4 g (24.6 mmol) of potassium hydroxide. The obtained mixture was refluxed for one hour, neutralized with dilute hydrochloric acid under cooling with ice, and extracted with ethyl acetate twice. The ethyl acetate phase was washed with water and dried over anhydrous magnesium sulfate. Then, ethyl acetate was distilled off in a vacuum. The residue was purified by silica gel column chromatography (solvent: dichloromethane/methanol) and recrystallizad from ethyl acetate to give 2.9 g of the title compound. Yield: 78.6%
m.p.: 188°~189° C.
M/Z (M+1)⁺: 451
¹H-NMR (DMSO-d₆)
δ(ppm)=0.83 (3H, t, J=7 Hz) 1.16 (3H, t, J=7 Hz) 1.20~1.40 (4H, m) 1.93 (3H, s) 2 01~2.16 (2H, m) 2.77 (2H, q, J=7 Hz) 2.99~3.08 (2H, m) 3.80 (2H, t, J=6 Hz) 4.10 (2H, t, J=6 Hz) 6.12~8.20 (1H, m) 6.54 (1H, d, J=7 Hz) 8.80 (1H, d, J=7 Hz) 7.11~7.60 (7H, m) 8.80 (1H, s)

Example 12

3-(2-Butylureido-3-methylphenoxy)propionic acid

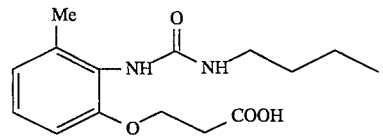

2.85 g (12.8 mmol) of N-butyl-N'-(2-hydroxy-6 -methylphenyl)urea and 0.73 g (13.0 mmol) of potassium hydroxide were dissolved in 2.5 ml of water. A solution of 0.70 g (6.5 mmol) of 3-chloropropionic acid in 1.5 ml of water and a solution of 0.35 g (6.3 mmol) of potassium hydroxide in 1 ml of water were simultaneously dropped into the solution prepared above at 70° C. The obtained mixture was stirred for 10 minutes, made acidic with dilute hydrochloric acid, and extracted with ethyl acetate twice. The ethyl acetate phase was extracted with an aqueous solution of sodium hydrogencarbonate and left standing to cause liquid-liquid separation. The aqueous phase was taken out and made acidic with dilute hydrochloric acid, and the acid aqueous phase was extracted with ethyl acetate twice. The ethyl acetate phase was washed with water and dried over anhydrous magnesium sulfate. Then, ethyl acetate was distilled off in a vacuum. The residue was recrystallized from ethyl acetate to give 120 mg of the title compound. Yield: 3.2%.
m.p.: 164°~165° C.
M/Z (M+1)⁺: 295
¹H-NMR (DMSO)
δ(ppm)=0.88 (3H, t, J=7 Hz) 1.20~1.40 (4H, m) 2.10 (3H, s) 2.68 (2H, t, J=6 Hz) 2.96~3.08 (2H, m) 4.10 (2H, t, J=6 Hz) 6.12~6.20 (1H, m) 6.75 (1H, d, J=7Hz) 6.82 (1H, d, J=7 Hz) 7.00 (1H, t, J=7 Hz) 7.08 (1H, s)

We claim:
1. A benzene derivative represented by the following formula (I) or a pharmacologically acceptable salt thereof:

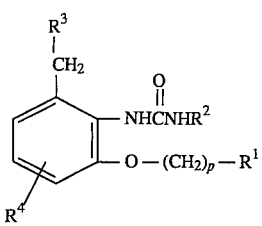

(I)

wherein R¹ represents a carboxyl group which may be protected or a group represented by the formula:

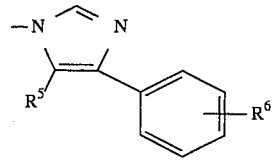

wherein R⁵ represents a lower alkyl group or a hydroxyalkyl group and R⁶ represents a hydrogen atom or a hydroxyl group;

R² represents a hydrogen atom, a lower alkyl group, a hydroxyalkyl group or a carboxyalkyl group;

R³ and R⁴ each represent a hydrogen atom or a hydroxyl group; and p is an integer of 1 to 6 with the proviso that when R⁴ is a hydrogen atom, and R² is a hydrogen atom or a lower alkyl group, R¹ is a carboxyl group which may be protected.

2. The benzene derivative or a pharmacologically acceptable salt thereof as set forth in claim 1, wherein R¹ in the formula (I) is a group represented by the formula:

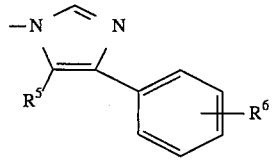

(wherein R⁵ represents a lower alkyl group or a hydroxyalkyl group and R⁶ represents a hydrogen atom or a hydroxyl group).

3. A benzene derivative represented by the following formula (I) or a pharmacologically acceptable salt thereof:

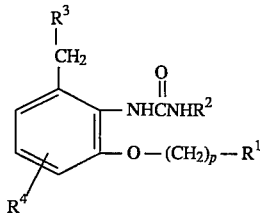

(I)

wherein R¹ is a carboxyl group which may be protected;

R² is a hydrogen atom or a lower alkyl group;

R³ is a hydrogen atom or a hydroxyl group;

R⁴ is a hydrogen atom; and is an integer of 1 to 6.

4. A benzene derivative represented by the following formula (I) or a pharmacologically acceptable salt thereof:

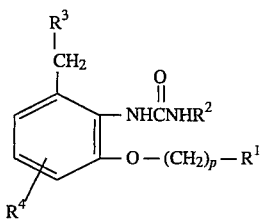

(I)

wherein R¹ represents a carboxyl group which may be protected or a group represented by the formula:

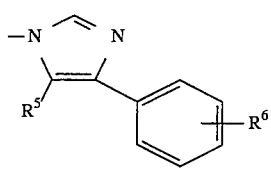

wherein R⁵ represents a lower alkyl group or a hydroxyalkyl group and R⁶ represents a hydrogen atom or a hydroxyl group;

R² represents a hydrogen atom, a lower alkyl group, a hydroxyalkyl group or a carboxyalkyl group;

R³ is a hydrogen atom or hydroxyl group;

R⁴ is a hydroxyl group; and p is an integer of 1 to 6.

5. A pharmacological composition comprising a therapeutically effective amount of a benzene derivative or a pharmacologically acceptable salt thereof as set forth in claim 1 and a pharmacologically acceptable vehicle.

6. A method for treating a disease for which a cholesterol O-acyl transferase inhibiting action is efficacious, which comprises administering a therapeutically effective amount of a benzene derivative or a pharmacologically acceptable salt thereof as set forth in claim 1 to a patient suffering from said disease for which a cholesterol O-acyl transferase inhibiting action is efficacious.

7. A method for treating arteriosclerosis which comprises administering a therapeutically effective amount of a benzene derivative or a pharmacologically acceptable salt thereof as set forth in claim 1 to a patient suffering from arteriosclerosis.

* * * * *